US011403965B2

(12) United States Patent
Dunbar et al.

(10) Patent No.: US 11,403,965 B2
(45) Date of Patent: Aug. 2, 2022

(54) SYSTEM AND METHOD FOR IMAGE-GUIDED PROCEDURE ANALYSIS AND TRAINING

(71) Applicant: eZono AG, Jena (DE)

(72) Inventors: Allan Dunbar, Jena (DE); Sungmo Lee, Jena (DE)

(73) Assignee: eZono AG, Jena (DE)

( * ) Notice: Subject to any disclaimer, the term of this patent is extended or adjusted under 35 U.S.C. 154(b) by 367 days.

(21) Appl. No.: 16/011,972

(22) Filed: Jun. 19, 2018

(65) Prior Publication Data

US 2018/0366035 A1 Dec. 20, 2018

(30) Foreign Application Priority Data

Jun. 20, 2017 (EP) .................................... 17176925

(51) Int. Cl.
*A61B 5/055* (2006.01)
*G09B 23/28* (2006.01)
(Continued)

(52) U.S. Cl.
CPC ............ *G09B 23/286* (2013.01); *A61B 5/055* (2013.01); *A61B 5/062* (2013.01); *A61B 6/037* (2013.01); *A61B 6/12* (2013.01); *A61B 8/0841* (2013.01); *A61B 8/4254* (2013.01); *A61B 8/463* (2013.01); *A61B 17/3403* (2013.01); *A61B 34/20* (2016.02); *G06T 7/10* (2017.01); *G06T 7/20* (2013.01); *G09B 23/285* (2013.01); *A61B 8/587* (2013.01); *A61B 2017/3413* (2013.01); *A61B 2034/107* (2016.02); *A61B 2034/2055* (2016.02); *G06T 2207/10016* (2013.01); *G06T 2207/10088* (2013.01);
(Continued)

(58) Field of Classification Search
None
See application file for complete search history.

(56) References Cited

U.S. PATENT DOCUMENTS

| | | |
|---|---|---|
| 6,263,230 B1 | 7/2001 | Haynor et al. |
| 6,733,458 B1 | 5/2004 | Steins et al. |
| 9,554,716 B2 | 1/2017 | Burnside et al. |
| 2008/0020361 A1* | 1/2008 | Kron ........................ G09B 5/02 434/262 |

(Continued)

FOREIGN PATENT DOCUMENTS

| | | |
|---|---|---|
| EP | 2 777 564 | 9/2014 |
| WO | WO 97/03609 | 2/1997 |

(Continued)

OTHER PUBLICATIONS

European Search Report dated May 11, 2018 issued in European Patent Application No. 17176925.0, 7 pp.

*Primary Examiner* — Bruk A Gebremichael
(74) *Attorney, Agent, or Firm* — Nixon & Vanderhye P.C.

(57) ABSTRACT

A system and method for quantitative validation of the quality of image-guided interventional procedures combine image data on the procedure with position tracking of the interventional instrument and calculate quantitative measures such as excursions of the interventional instrument from a desired position or track, procedure times and measurements of distances advanced and withdrawn. The quantitative metrics may be graphically displayed and stored. Metrics obtained for multiple users may be stored and statistically processed to derive measures of performance applicable to individuals or groups of clinicians.

28 Claims, 7 Drawing Sheets

(51) Int. Cl.
*A61B 6/12* (2006.01)
*A61B 6/03* (2006.01)
*A61B 5/06* (2006.01)
*A61B 8/08* (2006.01)
*G06T 7/10* (2017.01)
*G06T 7/20* (2017.01)
*A61B 17/34* (2006.01)
*A61B 34/20* (2016.01)
*A61B 8/00* (2006.01)
*A61B 34/10* (2016.01)

(52) U.S. Cl.
CPC ............... *G06T 2207/10104* (2013.01); *G06T 2207/10116* (2013.01); *G06T 2207/10132* (2013.01); *G06T 2207/30004* (2013.01); *G06T 2207/30241* (2013.01)

(56) References Cited

U.S. PATENT DOCUMENTS

| | | | |
|---|---|---|---|
| 2010/0298704 A1 | 11/2010 | Pelissier et al. | |
| 2011/0313429 A1* | 12/2011 | Anderson | A61B 17/322 606/131 |
| 2012/0189998 A1 | 7/2012 | Kruecker et al. | |
| 2014/0011173 A1* | 1/2014 | Tepper | A61B 8/4254 434/273 |
| 2016/0066794 A1* | 3/2016 | Klinder | A61B 5/02028 600/424 |
| 2016/0328998 A1* | 11/2016 | Pedersen | A61B 8/4245 |
| 2017/0200399 A1* | 7/2017 | Thomas | G06T 7/73 |

FOREIGN PATENT DOCUMENTS

| | | |
|---|---|---|
| WO | WO 2010/132985 | 11/2010 |
| WO | WO 2013/034175 | 3/2013 |

\* cited by examiner

| Input | 3D Chart | 2D Chart | Report | Control Variables | eZono Validation Software

Choose data File
Browse

☐ Upload to Cloud

UserName

UserLevel
Beginner

Supervisor Name

Applicants Name

Procedure Name

| Input | 3D Chart | 2D Chart | Report | Control Variables | eZono Validation Software

| Name | Value |
| --- | --- |
| User name | |
| Experience Level | Beginner |
| Supervisor Name | |
| Application Name | |
| Procedure Name | |

Quantitative Description

| Name | Value |
| --- | --- |
| INJECTION TYPE | IN PLANE |
| TOTAL TIME(s) | 28.8 |
| Pre-Puncture Time(s) | 1 |
| Puncture Time(s) | 27.1 |
| Distance tip travelled during puncture (mm) | 113.7 |
| Max. depth tip travelled during puncture (mm) | 26.9 |
| Ave./Std.dev. of needle inclination during puncture (deg.) | -33/2 |
| Ave./Std.dev. of needle direction during puncture (deg.) | 4/3 |

Safety & Quality Errors

| Name | Value |
| --- | --- |
| Number of significant trajectory readjustments | 2 |
| Distance travelled in reverse during each readjustment (mm) | 1:3mm, 2:9mm, |
| Number of times tip out of the image plane significant occurs (mm) | 2 |
| Distance tip travelled through the image plane each time (mm) | 1:16mm, 2:11m, |

SYSTEM AND METHOD FOR IMAGE-GUIDED PROCEDURE ANALYSIS AND TRAINING

CROSS-REFERENCES TO RELATED APPLICATIONS

This application claims the benefit of European Patent Application No. 17176925.0, filed Jun. 20, 2017, the entire content of which is herein incorporated by reference.

BACKGROUND

The present invention relates to the field of image-guided procedure analysis, particularly to systems and methods for analysis and quality validation of image-guided interventional medical procedures and to apparatus for training clinicians in image-guided interventional medical procedures.

There are numerous medical procedures that involve the insertion of an interventional tool or instrument, such as a needle, cannula, catheter, stylet, scalpel or other medical or surgical instrument, into a subject's body, e.g. minimally-invasive surgical procedures, regional anaesthesia, detection of bio-electrical signals, electrical stimulation for diagnosis or treatment, vascular access, fine needle aspiration, musculoskeletal injections and so on. In such procedures it is generally necessary to guide the interventional instrument properly to the desired position in the subject's body, and it can also be beneficial to monitor or track the interventional instrument position to ensure that it remains at the desired location. In general, it is very difficult for the user to determine the exact position of the tip of the interventional instrument and thus to be sure whether it is in the desired place, for example adjacent a nerve, or whether it has undesirably penetrated something else, for example a blood vessel.

A variety of technologies have been developed and commercialised for assisting clinicians in performing such interventional procedures on the human body. In particular, image-guided procedures, where the clinician can monitor the procedure using an imaging technology, such as ultrasound imaging (procedural ultrasound) or x-ray imaging, which gives a view of the internal anatomy of the patient's body, are available. These procedures may be further enhanced with a position detection system for tracking the interventional instrument. For example, U.S. Pat. No. 6,263,230 (Lucent Medical Systems, Inc.) discloses the use of x-ray imaging of a patient with magnetic tracking of a catheter tip to allow accurate positioning of a medical device such as a feeding tube in a patient's body. More systems have been developed which combine ultrasound imaging with some form of position tracking of an insertable interventional instrument because, unlike x-ray imaging, ultrasound imaging is safe for the patient and the clinicians for longer time, real-time use. Systems which disclose the combination of ultrasound imaging and position sensing of the instrument are disclosed in WO-A1-97/03609 (Paltieli), U.S. Pat. No. 6,733,458 (Acuson Corporation), WO-A1-2010/132985 (Ultrasonix Medical Corporation), and U.S. Pat. No. 9,554,716. These systems disclose that the position and track or trajectory of the insertable interventional instrument may be determined in a variety of ways, for example by using magnetic detection of the instrument or of magnetic markers attached to a hub of the instrument, or an optical system, possibly using optical markers on the instrument, electromagnetic position detection, or by using gyroscopic or accelerometric sensors. WO-A1-2013/034175 (eZono AG) discloses a system for monitoring an insertable interventional instrument such as a cannula, catheter or stylet by combining magnetic position detection of the interventional instrument with free-hand ultrasound imaging of the patient. The insertable interventional instrument is magnetised, or may carry a magnet or magnetic coating, and is detectable by magnetic field detectors integrated with the ultrasound imaging probe of the ultrasound imaging system. The magnetically-detected position and trajectory of the interventional instrument can be displayed on the ultrasound image display thus assisting the clinician in performing the interventional procedure accurately.

In the field of ultrasound imaging, point of care ultrasound has grown into a significant segment of the ultrasound market during the last 20 years. This has brought the benefits of ultrasound to many more patients through a wider base of non-traditional clinician users, but there has been a challenge in educating the non-traditional clinician users, and evaluating their skills. This is particularly true in the field of procedural ultrasound where, as mentioned above, ultrasound is used to guide insertion of a interventional instrument such as a needle, cannula, catheter, stylet etc. This has moved ultrasound imaging into new territory from a diagnostic tool used by specialists to a procedural aid potentially usable by a wide variety of clinician users. While ultrasound imaging brings the potential for a significant decrease in complications in interventional procedures, it introduces the need for a further skill, namely the skill involved in combining hand and eye co-ordination between the interventional instrument, such as the needle, and the ultrasound imaging probe, so that the interventional instrument is correctly positioned relative to the ultrasound image. For example, an in-plane needling procedure involves the clinician puncturing the skin of the patient and advancing the needle into the patient while keeping the needle in the plane of the ultrasound image (ultrasound images are typically in the form of a planar slice through the body, with the thickness of the plane being of the order of 1 mm thick). With skill the clinician can advance the needle to the desired position and back again while keeping it in the thin imaging plane and thus visible. However, excursions of the needle tip from the imaging plane mean that the tip becomes invisible in the ultrasound image, and advancing the needle in this state is potentially dangerous as the clinician does not know what is being penetrated. Alternatively, an out of plane injection involves advancing the needle at an angle to the ultrasound imaging plane. Usually in such a procedure the needle trajectory is roughly perpendicular to the image plane. These procedures may be used when injecting into a vein as it is difficult to conduct an in-plane procedure here, or when the target anatomy means that the needle path through the patient is much shorter if it is advanced at an angle to the imaging plane. In an out of plane procedure the user has no way to tell from the ultrasound image alone whether the needle tip has crossed right through the imaging plane as the needle is simply a white dot representing a cross section of the needle. If the needle tip crosses the plane it can be dangerous as it means the needle tip could puncture the back side of a vein which it is supposed to be in, could progress to puncture an artery which are typically close to veins or in a worst case could puncture the pleura and therefore cause pneumothorax. If the skills of co-ordinating the movement of the interventional instrument and the imaging probe are not learnt correctly, patient risk can increase in these procedures, instead of decreasing.

A vast effort has gone into educating the non-traditional clinician user base for point of care ultrasound with thousands of workshops and congresses worldwide, training from ultrasound equipment manufacturers, on the job training, e-learning and web pages and the like. The tools used for training are generally limited to presentation materials for theory, live model scanning for learning sono-anatomy, physical phantoms of all shapes, sizes and composition on which clinicians can learn needling techniques, and sometimes the use of cadavers for needling practice.

Despite these efforts, there is no clear evidence about the level of competence of users of image guided procedures. Experts in the field confirm that in their experience there is a large variation in skill level, particularly in relation to needling skills which are associated with a large patient risk. It would therefore be useful to provide reliable methods of determining whether users have had sufficient training, whether any particular training scheme is effective, how good are the skill levels of clinician users, how good is one organisation, e.g. hospital, compared to another and how well are image-guided procedures actually performed in reality.

Another problem is that it is expensive to devote point of care ultrasound apparatus to training. A significant amount of the training is concerned with the operator developing the hand-eye coordination and feel for manipulating an ultrasound probe in one hand, an interventional surgical instrument such as a needle or cannula in the other hand, while looking at a display showing the tracked instrument and the ultrasound image.

BRIEF SUMMARY

A first aspect of the present invention provides a system and method which stores the tracked position of an interventional instrument in an image-guided interventional procedure and processes the position data to derive one or more quantitative measures of the quality of the image-guided interventional procedure. In more detail, this aspect of the invention provides a system adapted to record and process data from an image-guided interventional procedure in which a interventional instrument is guided by an operator by reference to an image obtained by an imaging system and in which the position of the interventional instrument is tracked by a position tracking system, comprising: an input configured to receive position data representing the track of the interventional instrument during the image-guided interventional procedure from the position tracking system; a data store configured to record the position data; a data processor configured to process the position data to derive one or more quantitative measures of the quality of the image-guided interventional procedure; a display configured to display the one or more quantitative measures.

The processing to derive the one or more quantitative measures can be performed in real time, or can be performed as a post-procedure analysis. The processing can be performed by a data processor of the imaging system, or in a separate computer system or in a remote server connected to receive the position data over the Internet.

Preferably the system further comprises an input configured to receive image data from the imaging system and the data storage is configured to record the image data. Both the position data and image data are associated with time stamps which are stored and can be used to synchronise the display of the processed data. Preferably the data processor is configured to process the position data and image data together to derive the one or more quantitative measures of the quality of the image-guided interventional procedure. Thus the quantitative measures may depend only on position data, or may be based on a combination of the position data and image data.

The quantitative measures may, for example be spatial measurements related to the trajectory or track of the interventional instrument, such as the number of significant trajectory readjustments, the number of excursions of a tip of the interventional instrument from a desired trajectory or plane, such as the imaging plane of the imaging system, the distance advanced by a tip of the interventional instrument during excursions from the desired plane or trajectory, the number of incursions of a tip of the interventional instrument into an imaging plane of the imaging system, or the distance advanced through the imaging plane of the imaging system. The quantitative measure may alternatively, or in addition, be based on temporal measurements of the image-guided procedure, such as the puncture time (i.e. the time from initial puncturing of the patient's skin to removal of the instrument from the patient). The quantitative measures may be spatial or temporal deviations from a predefined procedure interventional instrument trajectory or procedure timing.

The data processor may be configured to derive other metrics related to information about the procedure, rather than its quality, such as the overall procedure time, the pre-puncture time, the insertion angle of the interventional instrument, the direction of movement of the interventional instrument relative to an imaging probe of the imaging system etc.

Thus with the invention, the storage and further processing of position data of the interventional instrument during the procedure allows consistent quantitative measures to be obtained relating to the quality of the procedure. For example, if the number of significant trajectory readjustments of the interventional instrument exceeds a small predefined threshold, for example two to four readjustments, this indicates that the clinician is hacking about in the patient, which can lead to pain, haematoma and infection. Being able to count the number of trajectory readjustments provides a reliable consistent measure which allows meaningful performance monitoring and meaningful comparisons between clinicians.

In an in-plane procedure where the interventional instrument is intended to advance in the imaging plane, determining the number of times the tip of the interventional instrument leaves the imaging plane gives a measure of the quality and skill level of the user, and determining the distance advanced by the tip of the instrument while it is out of the plane indicates whether the clinician was advancing the instrument while effectively blind to its position. This is dangerous as it can lead to complications, such as accidental puncturing of a blood vessel. Similarly, in an out-of-plane procedure where the interventional instrument is advanced at an angle to the imaging plane, counting the number of times the interventional instrument passes through the imaging plane, and the distance advanced, again provides a reliable measure of the skill level of the clinician and level of risk of the procedure.

The data processor may process the image data and position data together to derive how many times the imaging probe has moved during the procedure as too much motion of the imaging probe during a procedure is indicative of a poor skill level and leads to an extended procedure time and risk of advancing the interventional instrument without proper visualisation of the patient's anatomy.

Quantitative measures of the puncture time and number of punctures give a clear indication of the likely level of pain, risk of infection and risk of haematoma suffered by the patient.

The quantitative measures may be displayed graphically, for example by displaying the measured position of the tip of the interventional instrument relative to an imaging plane of the imaging system against elapsed time of the procedure. Further, the display may be colour coded with the direction of movement of the interventional instrument, for example tip positions during advancement of the interventional instrument may be coloured green and tip positions during withdrawal of the interventional instrument coloured red. This gives a quick visual indication of how the instrument was moved during the procedure and the degree of movement compared with the in-plane or out-of-plane position of the instrument tip.

A three-dimensional visualisation of the procedure can be displayed showing the track or trajectory of the tip of the interventional instrument, colour coded as above, either displayed in isolation or against a representation of the patient's anatomy derived from the imaging system. Alternatively, or in addition, plan views from above the imaging probe or in the longitudinal direction of the interventional instrument can be displayed.

Tables and spider charts may be used to display numerical and descriptive data.

Preferably the data store is configured to record the stored data with the identity of the operator of the procedure (clinician) and organisation, and preferably patient data. This allows statistical analysis of procedures based on identity of the clinician or identity of the organisation. This allows comparison between different user groups, monitoring changes in performance over time, benchmarking for levels of performance and the effectiveness of different training regimes.

The imaging system is preferably a freehand ultrasound imaging system, but the invention may also be used with an x-ray imaging system, magnetic resonance imaging system, PET imaging system as the recordal and processing of accurate position data of the interventional instrument allows the calculation of quantitative performance metrics regardless of the specific type of imaging system.

The position tracking system may be a magnetic position detection system, optical position detection system, or electromagnetic position detection system, for example using any of the position tracking systems mentioned in the introduction. Thus, in one example, the interventional instrument may be magnetised (or may carry permanent magnets or a magnetic coating), and its position be tracked by means of magnetic field detectors mounted to an imaging probe of the imaging system. eZono AG, for example, provide a combined magnetic tracking and ultrasound imaging system in which the magnetic field detectors are incorporated in the freehand ultrasound imaging probe and the magnetically-detected position of the interventional instrument is displayed on the ultrasound image itself and the invention may be employed in such a system.

The quantitative measures may be based on the trajectory of the interventional instrument compared to a frame of reference based on the imaging system, for example an imaging plane of the imaging system, but alternatively, or in addition, the data processor may be configured to receive image segmentation information relating to the structure of the subject in the image (e.g. the anatomy of the patient) and to derive one or more quantitative measures relating to the trajectory of the interventional instrument relative to the structure of the image subject. The image segmentation information may be provided by input from a skilled user observing the image, or may be obtained by automatic image processing of the image. Such structure-based quantitative measures can indicate, for example, whether the interventional instrument has entered the correct part of a patient's anatomy (for example the front of a vein rather than the back of a vein), or whether it has been correctly positioned relative to the anatomy (for example in regional anaesthesia it is important that the tip of the needle should be close to a nerve, but not puncture a nerve). Further quantitative measures can be derived, such as if a back wall of blood vessel has been punctured, by how far did the interventional instrument go beyond the back wall, how many times has some structure been punctured.

The system may further comprise an input for receiving a video image of the user conducting the image-guided interventional procedure. For example, a video camera such as a low cost webcam can monitor the user, providing useful additional information about their skill level. The system can include eye tracking of the user, thus providing more information about the user's skill level as it is important that the user focuses mainly on the image obtained by the imaging system rather than the interventional instrument itself.

The system may further comprise a physical phantom representing a patient's anatomy, this being useful for training purposes. Physical phantoms will have a known anatomy making it easy to perform image segmentation and provide more accurate quantitative measures of the trajectory and positioning of the interventional instrument relative to the anatomy. The physical phantom may be internally instrumented with a video camera (video endoscope) which provides additional video confirmation of whether the interventional instrument is in the correct part of the phantom's anatomy.

The invention may be embodied in the form of a separate system which receives position data and image data, or the system may be integrated with the imaging system or with the position tracking system, or all three may be integrated together in a single system.

The invention therefore also provides a method of recording and processing data from an image-guided interventional procedure, which method is executed in a dedicated system or in an imaging or position detection system or integrated system. The invention also provides a computer program for controlling a computer system to execute the method of the invention. Such a computer program may be embodied as a tangible or non-tangible computer program product.

In a second aspect the invention provides a non-imaging training apparatus for training image-guided interventional procedures, the apparatus comprising: a controller; a display connected to the controller for displaying a stored representation of an ultrasound image; a handset; the handset incorporating a non-imaging position detection system for detecting the position and orientation of an interventional instrument, the detection system being connected to the controller; the controller being adapted to display on the representation of an ultrasound image the position and orientation of the interventional instrument relative to the handset.

The training apparatus is therefore capable of replicating the feel of an image-guided interventional procedure, without the expense of an imaging system.

The position detection system may be a magnetic or optical position detection system, for example a magnetic position detection system comprising magnetic field sensors mounted internally of the handset and which detect the magnetic field of a magnetic interventional instrument in the manner and using the techniques described in WO 2013/034175. Preferably the handset comprises a casing or shell of a handheld ultrasound probe so that it replicates exactly the feel of an ultrasound image guided system.

The training apparatus may include a physical phantom representing a patient's anatomy and one or more magnetized interventional instruments, such as cannulae.

Preferably the training apparatus comprises an image store storing plural representations of ultrasound images. The controller is adapted to select one of the stored representations for display, optionally under the control of the operator. The stored representations may be of images of different parts of a human anatomy, and/or from different viewpoints.

BRIEF DESCRIPTION OF THE DRAWINGS

The invention will be further described by way of example with reference to the accompany drawings in which.

DETAILED DESCRIPTION

Figure 1:
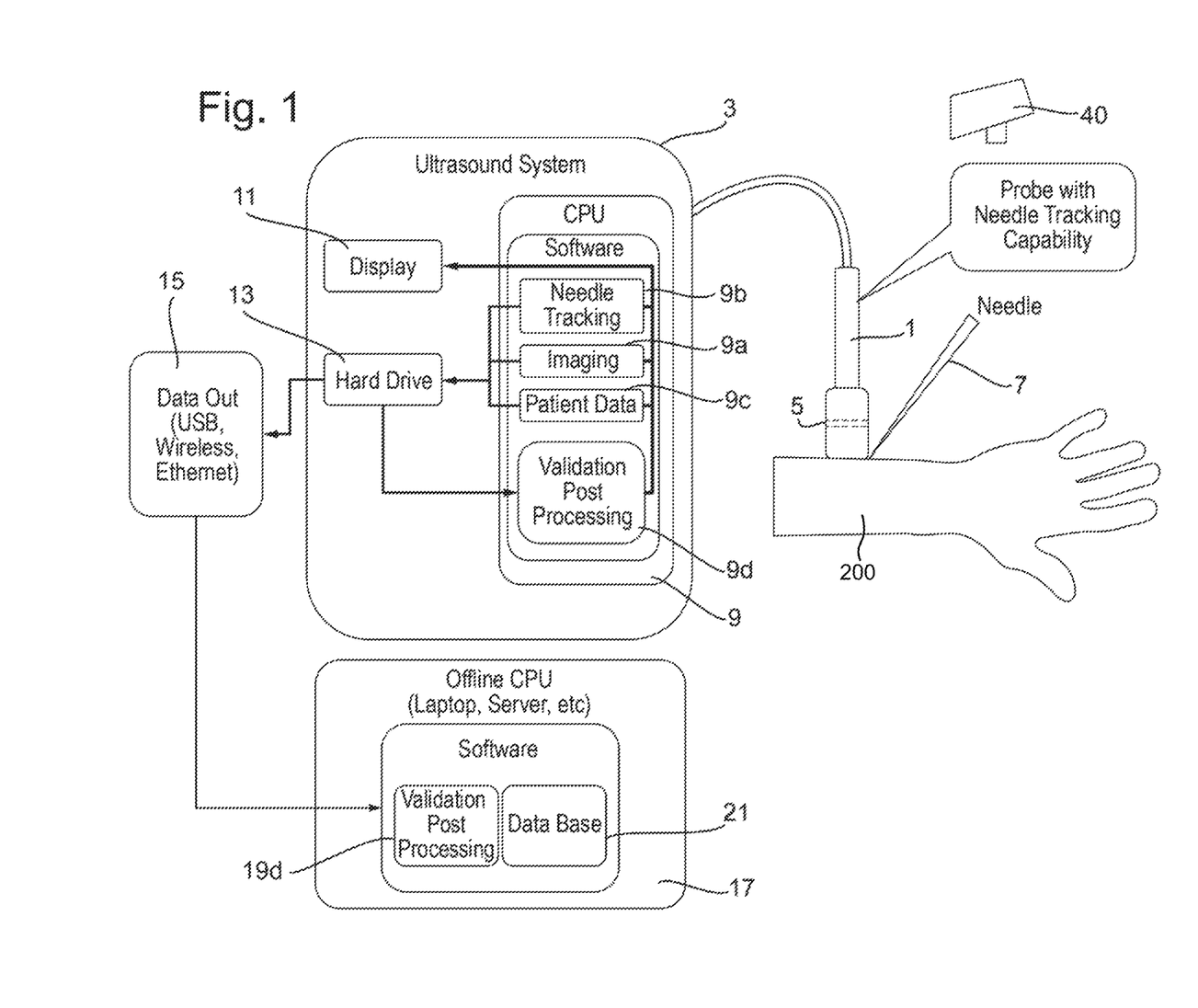
FIG. 1 schematically illustrates a system in accordance with an embodiment of the invention.

FIG. 1 schematically illustrates an embodiment of the invention applied to an ultrasound image-guided procedure using a system combining ultrasound imaging and magnetic tracking, such as disclosed by WO-A1-2013/034175 (eZono AG). As illustrated in FIG. 1, the imaging system comprises a freehand ultrasound imaging probe 1 which is controlled by and supplies ultrasound data to a combined ultrasound and position detection system 3. The ultrasound imaging probe 1 also includes a plurality of magnetic field detectors in a magnetic detector array 5 which detect the magnetic field from the interventional instrument 7 (in this case a magnetised needle), and supply magnetic field measurements to the combined ultrasound and position detection system 3.

The combined ultrasound and position detection system 3 includes a data processor 9, display 11 and data store 13 (which may be in the form of a disk drive or solid state hard drive). It optionally also includes a data output 15 (such as USB, wireless or Ethernet) for supplying data on the procedure to a remote station 17.

The ultrasound probe 1, data processor 9 and display 11 may operate in a standard two-dimensional B-mode ultrasound manner with the processor 9, which is connected to the ultrasound probe 1 via a cable, driving an ultrasound transducer in the ultrasound probe 1 by sending electrical signals to cause it to generate ultrasound pulses, and interpreting the raw data received from the ultrasound transducer, which represent echoes from the subject's body 200, to assemble it into an image of the patient's tissue and to display that image on the display 11.

The magnetic detection array 5 may be integral with or detachably attached to the ultrasound probe 1 and can be battery-powered or powered from the system 3. The magnetic detection array 5 may be connected by a wireless connection or wired connection to the system 3 and the processor 9 includes a position detection system 9b for processing the magnetic field measurements and deriving from them the position and orientation of the interventional instrument 7 relative to the imaging probe 1. The processing is as described in detail in WO-A1-2013/034175 and provides the position in three dimensions (x, y, z) of the tip of the interventional instrument and either the position in three dimensions (x, y, z) of the tail of the interventional instrument, or the orientation ($\varphi$, $\theta$) of the interventional instrument.

In this specification, by interventional instrument is meant any medical instrument which is insertable into a patient such as needle, cannula, catheter or stylet, or any instrument used in as surgical procedure such as a scalpel.

By the "track" or "trajectory" of such an instrument is meant the set of positions the instrument, or a part of the instrument, such as the tip, occupies through the procedure and the timing in those positions, e.g. the path which the needle tip has followed spatially during the procedure, as obtained by a position detection or tracking system.

The imaging system 9a receives the position data from the position tracking system 9b and superimposes a representation of the interventional instrument and/or the projected track of the interventional instrument on the display 11.

Figure 2:
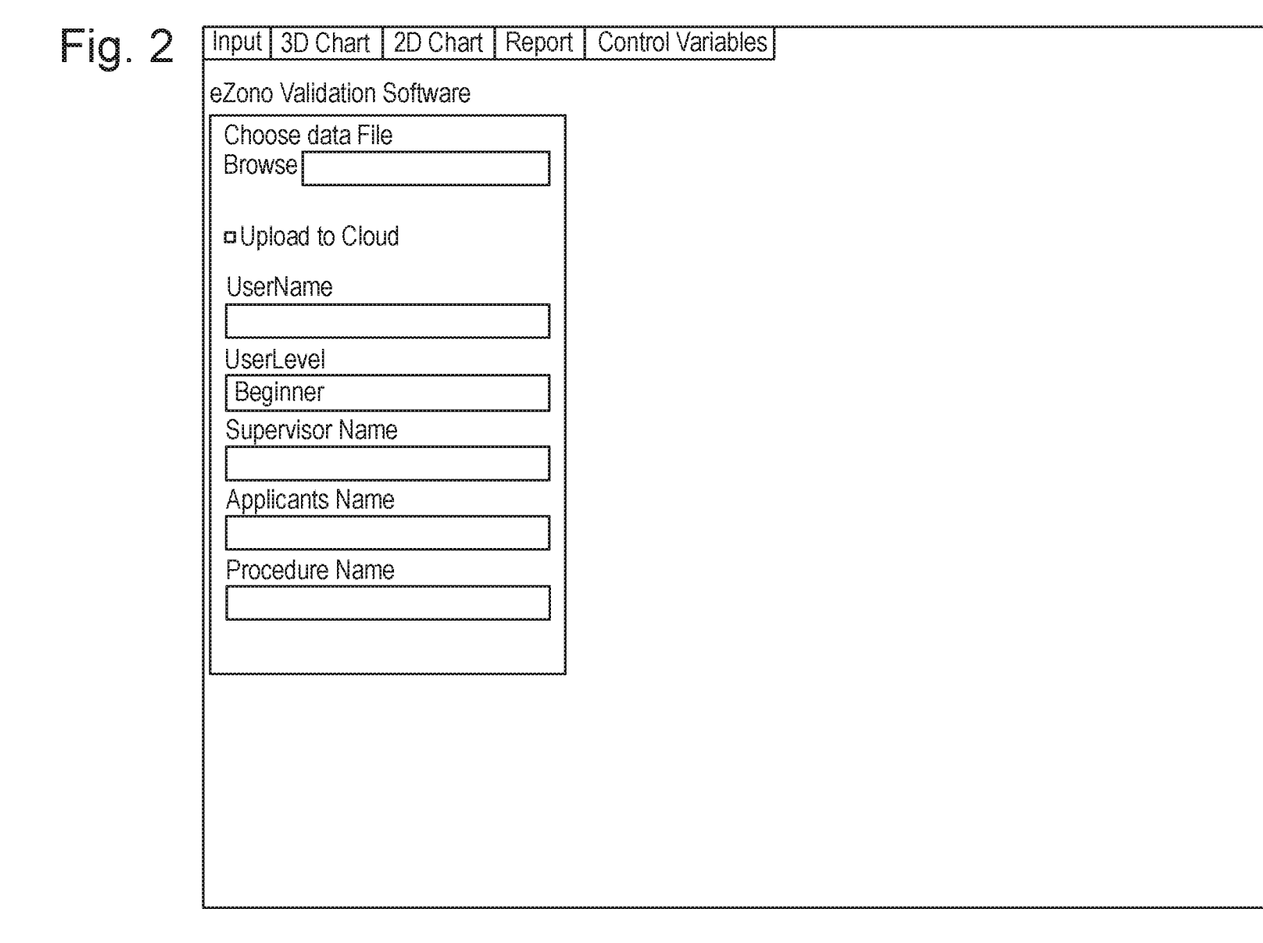
FIG. 2 illustrates one example of a user interface for input of data in one embodiment of the invention.

The position data and imaging data from the imaging system 9a and position detection system 9b are also stored on the data store 13 together with patient data, and optionally clinician, organisation and procedure data input using a data input interface 9c which can present to the clinician a data input form exemplified in FIG. 2.

The image probe position may also be detected and stored. The] [imaging probe position can be found in many ways: e.g. a separate tracking system specifically for the imaging probe; analysis of temporal image stream output from the ultrasound system; algorithms that analyse the needle guidance data and derive the probe movement(such an algorithm can be implemented as part of needle guidance data analysis).

The data processor 9 includes a processing capability 9d for processing the positioning data, optionally with the image data, to obtain a variety of quantitative measures of the quality of the procedure. These may be obtained and displayed in real time on the display 11, or may be obtained in a post-procedure procedure process.

As the position of the tip of the interventional instrument 7 relative to the imaging probe 1 is measured throughout the procedure, the validation processing can return safety and quality error metrics represent safety critical issues, and also descriptive information metrics which are useful to record, but not safety-critical.

As descriptive information metrics, in this embodiment the following are recorded: injection type, total procedure time, pre-puncture time (namely from switching on the system to puncturing the patient's skin), puncture time (namely the time from puncturing the patient's skin to the interventional instrument being withdrawn from the patient), insertion angle (i.e. angle of needle relative to the skin surface), the direction of the interventional instrument relative to the imaging probe 1.

As safety and quality error metrics or quantitative measures of procedure quality, this embodiment of the invention provides the following:

I) The number of significant trajectory readjustments—many significant trajectory readjustments means that the clinician is "hacking about" in the patient which can lead to pain, haematoma and infection. "Significant" is related to the size of the readjustment and what the procedure is. For example a readjustment of over 5 mm would likely be considered as too much by experts in the field. The threshold regarded as too many also depends on the procedure and is settable in the system, but it may typically be around 2 to 4.

II) For long axis, (in-plane procedures)—the number of times the tip of the interventional instrument goes outside the ultrasound image plane.

III) For long axis, (in-plane procedures)—for each excursion out of the image plane, what is the distance advanced by the tip of the interventional instrument during that excursion; this, together with the number of excursions, indicating to what extent the clinician is advancing the interventional instrument while effectively blind because the instrument is out of the imaging plane.

IV) For short axis, (out-of-plane procedures)—the number of times the tip of the interventional instrument goes through the ultrasound image plane.

V) For short axis, (out-of-plane procedures)—for each crossing of the imaging plane, the distance advanced through the plane by the tip of the interventional instrument. The number of crossings of the image plane and distance advanced again given indication of the extent to which the clinician is operating effectively blind.

VI) Imaging probe motion: how many times has the probe been moved during the procedure. At the moment one or two image probe movements are regarded as normal while more than five are regarded as indicative of poor performance. A movement of the probe is regarded as rotations of substantially 10 degrees or more or translations of substantially 5mm or more. Thresholds for these may be made settable in the system.

VII) Amount of probe motion—too much motion of the imaging probe indicates a poor skill level of the clinician and leads to an extended procedure time and risk of the interventional instrument being advanced without adequate visualisation using the imaging system.

VIII) Puncture time—if the overall puncture time is too long it can increase the risk of pain, infection and haematoma.

IX) Number of punctures; if the clinician punctures the patient multiple times it obviously increases the discomfort and risk of infection.

The thresholds mentioned above may be used to when the analysis results are displayed, e.g. by displaying in a visually-distinguishable way (e.g. by colour-coding) results that exceed the thresholds.

The invention thus provides a number of reliable, repeatable, quantitative measurements of the quality of the image-guided procedure which have consistent meaning across different procedures. These measurements may be used to monitor the effectiveness of training, the progress of the clinician, continuing performance evaluation, comparison across groups in different organisations and so on.

As illustrated schematically in FIG. 1 the data stored by the data store 13 may be output using interface 15 to a remote station 17 in the form of a remote server. This may store data from multiple users and organisation in a database 21 and it may perform statistical analysis using its validation processor 19d which obtains information and error metrics as above and also statistically analyses them.

Figure 3:
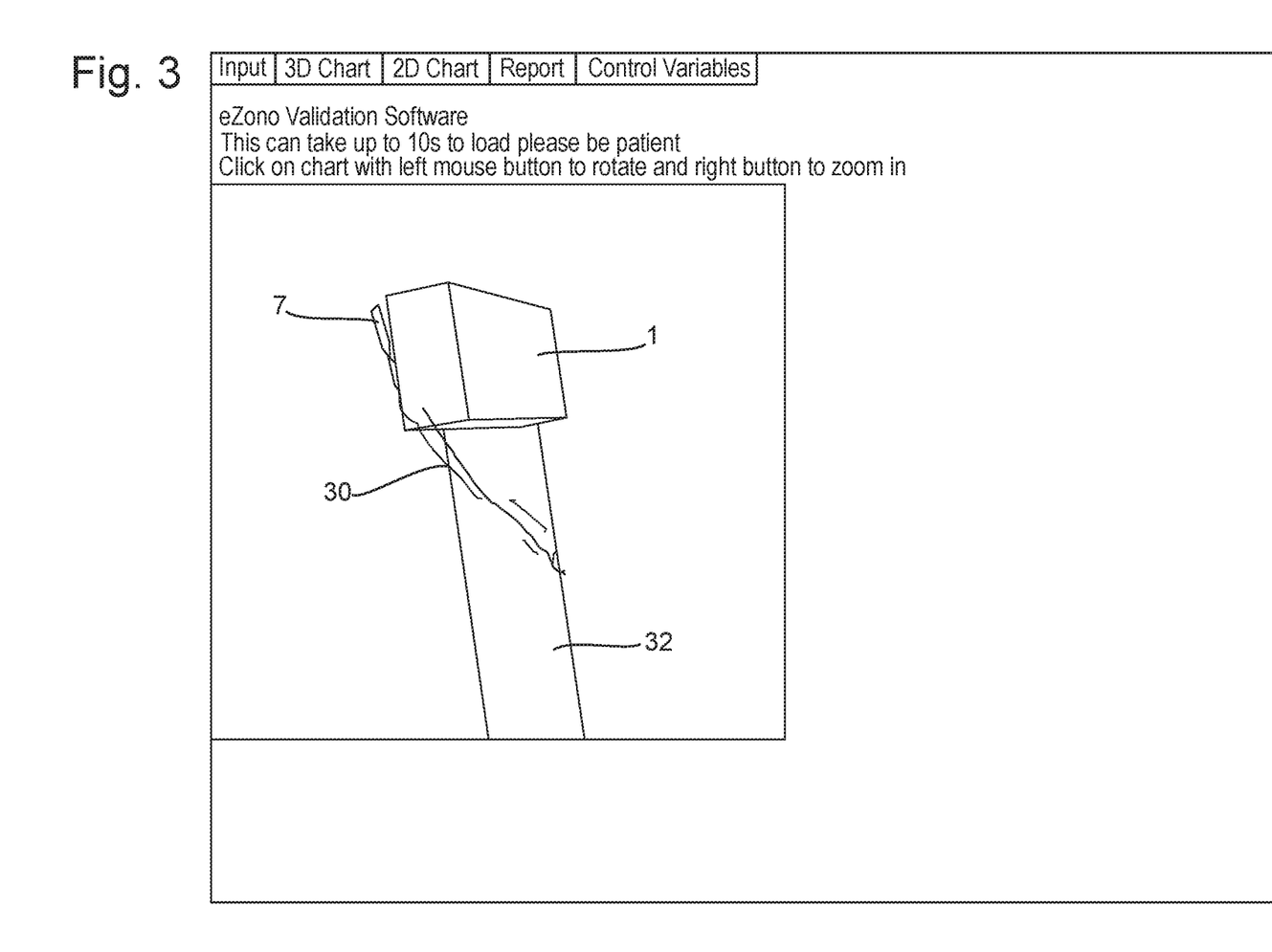
FIG. 3 illustrates an example of a three-dimensional visualisation of a procedure obtained with an embodiment of the invention.

The information and error metrics and the data stored from the procedures may be displayed in a variety of ways. FIG. 3, for example, shows a schematic three-dimensional display of a single ultrasound image-guided needling procedure with the track 30 of the needle 7 graphically indicated relative to the imaging plane 32 of the ultrasound transducer 1. Preferably positions in the track 30 associated with an advancing needle tip are colour coded green, and positions associated with a retreating needle tip colour coded red, this giving a quick and clear visualisation of the smoothness, accuracy and quality of the procedure.

Figure 4:
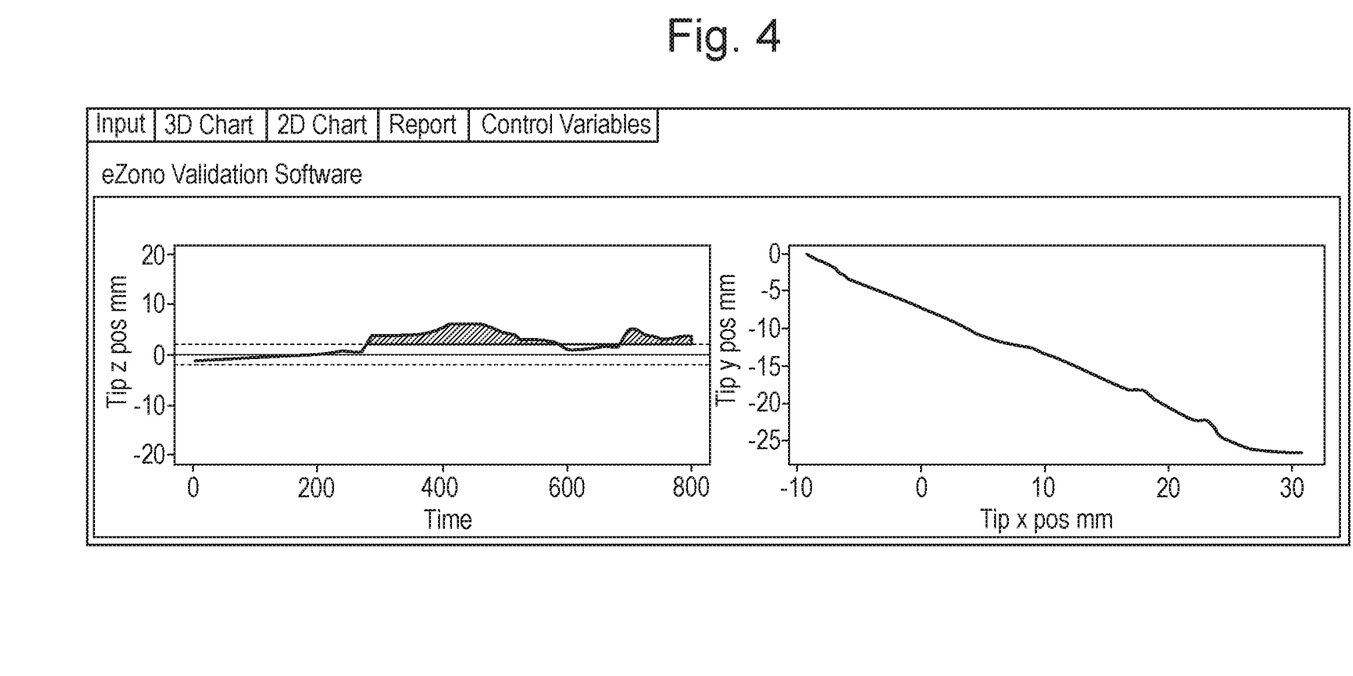
FIG. 4 schematically illustrates two graphical plots of quantitative metrics of an image-guided procedure obtained with an embodiment of the invention.

FIG. 4 illustrates two graphical plots of quantitative measures obtained in accordance with the embodiment of the invention above. In the left hand plot of the z-position of the needle tip (i.e. its distance orthogonally from the imaging plane 32) is plotted against procedure time. As with the display in FIG. 3, positions associated with an advancing needle tip may be colour coded green and with a retreating needle tip colour coded red. Furthermore, thresholds representing too great an excursion from the imaging plane may be graphically indicated and needle positions associated with such large excursions further colour-coded (e.g. with a solid infill below the displayed position). The right hand plot in FIG. 4 illustrates a graphical plot of the x and y positions of the needle tip during the procedure (the x axis is aligned with the projection direction of ultrasound energy into the patient and the y direction is laterally in the imaging plane). Again red and green colour-coding may be used to indicate positions associated with retreating and advancing needle movements respectively.

Figure 5:
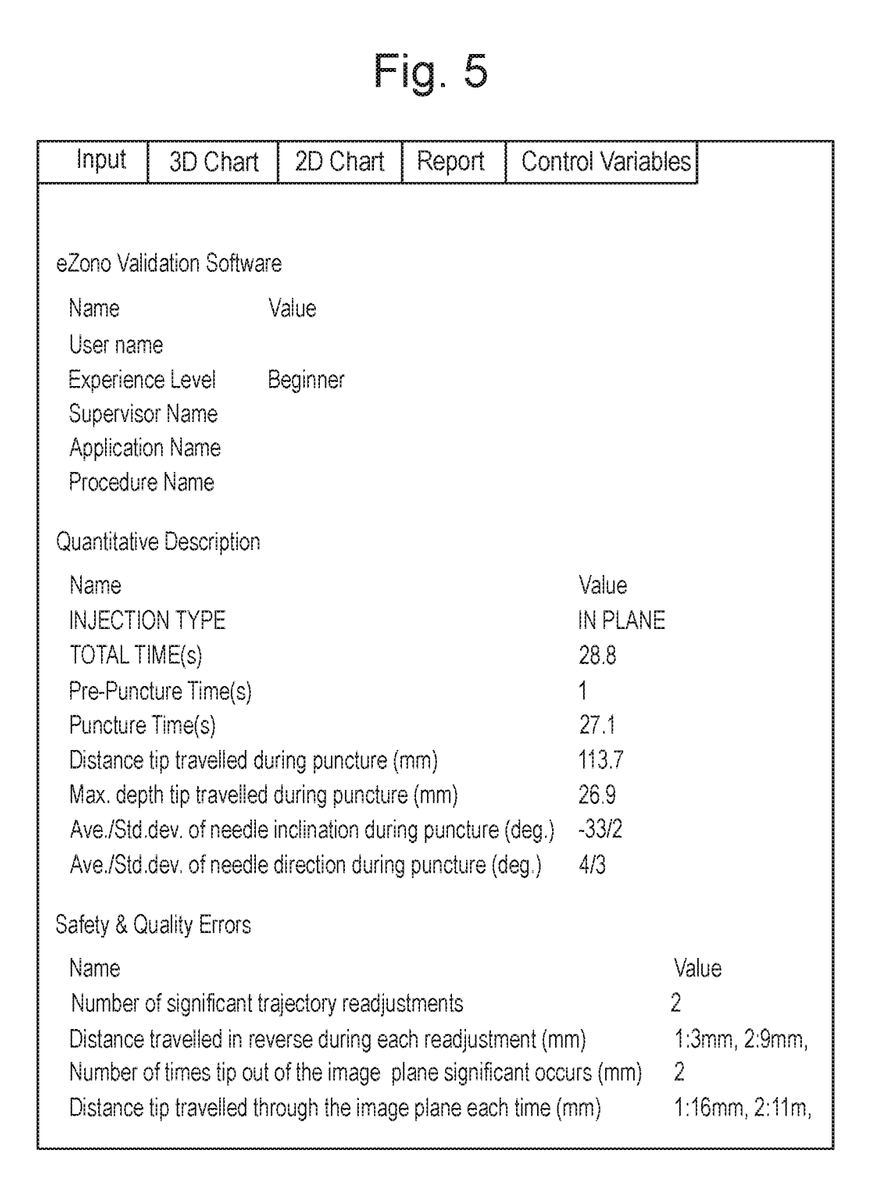
FIG. 5 is an example of an output form for numerical quantitative metrics obtained for a procedure in accordance with an embodiment of the invention.

As well as graphical displays the quantitative measures may be assembled into a procedure form such as that illustrated in FIG. 5, this noting information relating to the clinician and their experience level, the type of procedure, the total time, pre-puncture time, puncture time of the procedure, the distance travelled by the tip of the interventional instrument and the maximum depth of penetration, together with statistical measures (average or standard deviation) of the needle inclination and direction during the puncture. The significant safety and quality error metrics such as number of significant trajectory readjustments, distance travelled in reverse during each readjustment, number of times out of plane and distance travelled while out of plane may also be indicated.

As well as recording the position of the interventional instrument relative to the imaging plane of the imaging system, the system may also provide information regarding the position of the interventional instrument relative to the patient's anatomy. To achieve this, image segmentation information, which can be automatically obtained by processing of the image or input by a skilled user observing the image, is provided to the processor 9 which, knowing the position of the interventional instrument relative to the ultrasound image, can then quantify errors in the positioning of the interventional instrument relative to the anatomy. For example, it could determine whether a clinician made a back wall puncture of a vein, and if so how far did the tip of the interventional instrument go beyond the vein back wall. It could quantify how many times the user punctured a vein or other part of the anatomy unintentionally.

The system may further include a video camera 40, such as a low cost webcam, for videoing the clinician performing the procedure and this video image may be stored in the data store 13 and optionally sent to the remote database 21. The video can be processed to provide user eye motion tracking so that an indication can be obtained of whether the user is using the image guiding system correctly—i.e. viewing the image on the display 11 rather than looking at the interventional instrument 7.

Figure 6:
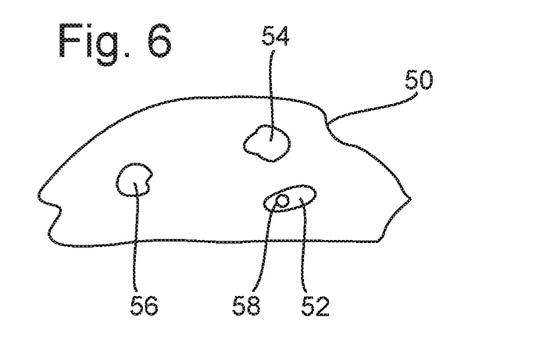
FIG. 6 schematically illustrates a physical phantom usable in an embodiment of the invention.

The system may also include a physical phantom 50 schematically illustrated in FIG. 6. Typically such phantoms are made of silicone rubber and include parts representing typical anatomical structures such as veins 52, arteries 54 or organs 56. The phantom may be internally instrumented with a video endoscope 58. The phantom 50 is usable in a training procedure in which the user images the phantom 50 using the imaging probe 1 while inserting a interventional instrument 7. The progress of the interventional instrument may be monitored from inside the phantom using the video endoscope 58. As phantoms have a known anatomy, it is easier to perform image segmentation and as each phantom type is the same, the same image segmentation applies so consistent quality measures can be recorded.

The data recorded in the systems of the invention, the image data, position data and optionally video data, can be displayed to the user in a visualisation process, for example with an "action replay" when errors occur.

The variety of quantitative measures may be combined into a single score for a procedure, for example by allocating point scores to each error, these accumulating or being subtracted from a perfect score.

Figure 7:
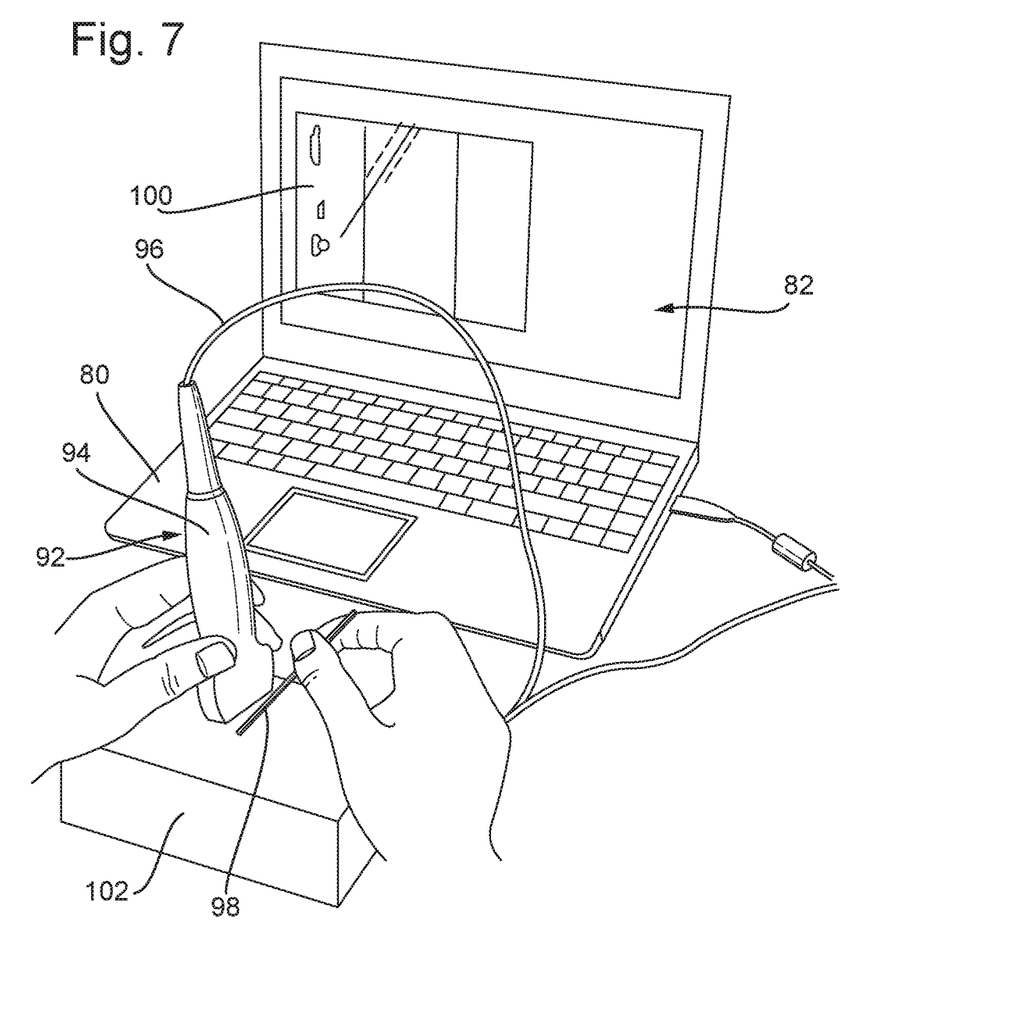
FIG. 7 schematically illustrates a training apparatus according to another embodiment of the invention.
Figure 8:
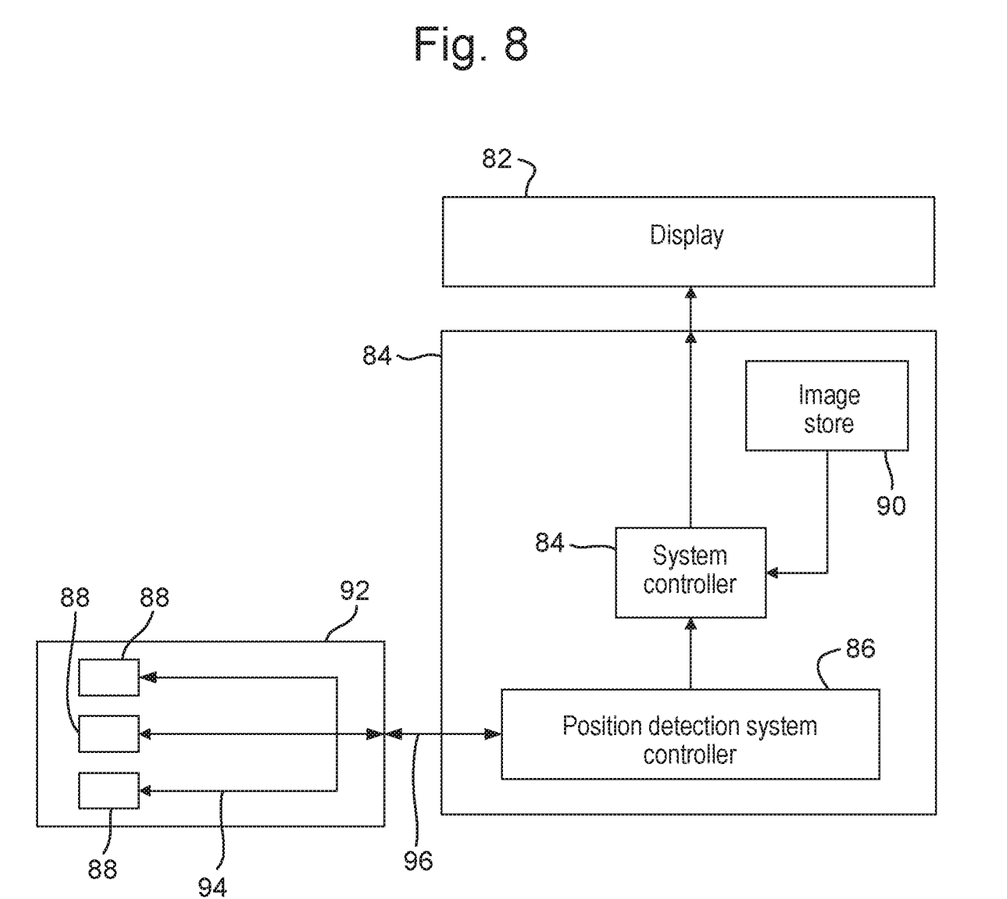
FIG. 8 is a block diagram of the functional parts of the training apparatus of FIG. 7.

FIGS. 7 and 8 schematically illustrate a non-imaging training apparatus for use in training image-guided interventional procedures in accordance with an embodiment of the invention. The training apparatus is designed and configured to allow a user to develop and practice the skills of manipulating an ultrasound imaging probe and an interventional instrument while observing a display showing an ultrasound image and the detected position of the interventional instrument, without the expense of a fully-fledged ultrasound imaging apparatus. The training apparatus in this embodiment therefore comprises a handset 92 connected by a cable 96 to a controller 80, which in this embodiment is a programmed laptop computer. The handset 92 is constituted by a casing or shell 94 of a handheld ultrasound imaging probe, without its imaging components (such as piezoelectric transducers and drivers therefore), but which does include a position detection system for detecting the position and orientation of the interventional instrument 98 such as a cannula. The position detection system may be a magnetic position detection system or an optical position detection system of the type well-known in the art and mentioned in the introduction above. For example, a magnetic position detection system which includes plural magnetometric detectors 88 controlled by a position detection system controller 86 may be used of the type disclosed in WO 2013/034175 (eZono AG) which is incorporated herein by reference. In this case the interventional instrument 98 is magnetized and, as explained in WO 2013/034175, the magnetometric detectors 88 detect the combination of the magnetic field from the interventional instrument and the ambient magnetic field (e.g. the terrestrial magnetic field and any stray magnetic fields around), and the position detection system controller 86 processes the measurements from the magnetometric detectors 88 to derive the position and orientation of the interventional instrument 98 relative to the handset 92. This detected position and orientation is supplied to the system controller 84 for display on display 82.

The system controller 84 is also adapted to take an image from an image store 90, the image being a representation of an ultrasound image of a patient's anatomy. The stored images may be screenshots from actual ultrasound scans of a patient, or may be artificial/schematic representations of such an ultrasound image. Optionally there may be several images available of different parts of a patient's anatomy, from different viewing directions, and the user can be provided with the option of selecting the desired image for display. As illustrated in FIG. 7, the ultrasound image is displayed with the detected position and orientation 100 of the interventional instrument 98 graphically superimposed over the representation of the ultrasound image. As the interventional instrument 98 is moved relative to the handset it will be tracked by the position detection system and so the corresponding movement will be shown on the display. The representation of the ultrasound image is fixed (as it is just a stored image), but the operator can get the feel of controlling movement of the interventional instrument 98 while holding the handset and watching the display 82.

The display 82 may also comprise stylised or iconic representations of the position and orientation of the interventional instrument 98 alongside the representation of the ultrasound image. For example, in FIG. 7, three such stylised representations are displayed on the left-hand side of the display 82.

The display 82 preferably further comprises a panel for the user to make control and selection inputs, this being illustrated on the right-hand side of the display in FIG. 7.

While FIG. 7 illustrates the controller 80 as a laptop computer incorporating display 82, the system may use any other forms of programmable controller such as a desktop computer with a separate display, or may use a dedicated device operating the position detection system and combining its output with a displayed representation of an ultrasound image.

The training apparatus also includes a physical phantom 102 which can be more or less representative of a patient's anatomy. At its simplest, the phantom 102 can be a block of elastomeric material which provides a similar feel to the operator as when performing an interventional procedure such as needling on the human body, or it may be a phantom which includes different internal structures, such as that previously illustrated in FIG. 6.

The advantage of the training apparatus is that although it replicates the feel of an ultrasound imaging system, and allows the user to practice the movements required for holding an ultrasound imaging probe while performing an interventional procedure and observing a display, the apparatus is a non-imaging apparatus, in that it does not include an imaging system in the handset, nor any imaging software in the controller 80. It therefore provides a cheap and economical system on which operators can be trained and can improve their skills.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and scope of the appended claims.

The invention claimed is:

1. A system adapted to record and process data from an image-guided interventional procedure in which an interventional instrument is guided by an operator by reference to an image obtained by an imaging system and in which the position of the interventional instrument is tracked by a position tracking system, comprising:
- an input configured to receive position data representing the track of the interventional instrument during the image-guided interventional procedure from the position tracking system;
- a data store configured to record the position data;
- a data processor configured to process the position data to derive one or more quantitative measures of the quality of the image-guided interventional procedure; and
- a display configured to display the one or more quantitative measures, wherein:
- the display is configured to display a graphical plot of a position of a tip of the interventional instrument relative to an imaging plane of the imaging system against elapsed time in the procedure to show a trajectory of the tip, and the display is configured to color code the trajectory according to a direction of movement of the interventional instrument, the color coding being such that a part of the trajectory when the tip is advancing towards the imaging plane is colored with a first color and a part of the trajectory when the tip is retreating from the imaging plane is colored with a second color, the first color being different from the second color;
- the data processor is configured to derive spatial or temporal measurements of a trajectory of the interventional instrument as said one or more quantitative measures, and wherein the quantitative measures are at least one of:
  - number of significant trajectory readjustments,
  - number of excursions of the tip of the interventional instrument from the imaging plane of the imaging system,
  - distance advanced by the tip of the interventional instrument during excursions from the imaging plane of the imaging system,
  - number of incursions of the tip of the interventional instrument into the imaging plane of the imaging system,
  - distance advanced through the imaging plane of the imaging system,
  - number of times an imaging probe of the imaging system moved,
  - puncture time, and
  - number of punctures.

2. The system according to claim 1 further comprising:
- an input configured to receive image data from the imaging system;
- the data store is configured to record the image data; and
- the data processor is configured to process the position data and image data to derive the one or more quantitative measures of the quality of the image-guided interventional procedure.

3. The system according to claim 2 wherein the position data and image data are each associated with time stamps to permit them to be mutually synchronized.

4. The system according to claim 1 wherein the data processor is configured to derive spatial deviations from a predefined interventional instrument trajectory as said one or more quantitative measures or to derive temporal deviations from a predefined procedure timing as said one or more quantitative measures.

5. The system according to claim 1 wherein the data processor is configured to process the position data to derive one or more information metrics relating to the image-guided procedure.

6. The system according to claim 5 wherein the information metrics comprise at least one of: procedure time, pre-puncture time, puncture time, insertion angle of the interventional instrument, direction of movement of the interventional instrument relative to the imaging probe of the imaging system.

7. The system according to claim 1 wherein the display is configured to display graphical plots of the one or more quantitative measures.

8. The system according to claim 1 wherein the imaging system is one of: an ultrasound imaging system, x-ray imaging system, magnetic resonance imaging system, a PET imaging system.

9. The system according to claim 1 wherein the position tracking system is one of: a magnetic position detection system, or an optical position detection system.

10. The system according to claim 1 wherein the position tracking system is a magnetic position detection system comprising magnetic field sensors mounted to the imaging probe of the imaging system and a magnetic field of the interventional instrument.

11. The system according to claim 1 wherein the data processor is configured to receive image segmentation information relating to the structure of the subject of the image and to derive said one or more quantitative measures relative to the structure of the subject of the image.

12. The system according to claim 11 wherein the data processor is configured to process the image obtained by the imaging system to automatically generate said image segmentation information.

13. The system according to claim 1 further comprising an input configured to receive a video image of the operator conducting the image-guided interventional procedure, wherein the video image is processed to provide user eye motion tracking.

14. The system according to claim 1 further comprising a physical phantom representing a patient's anatomy, the physical phantom being internally instrumented with a video camera, the data store being configured to record the output of the video camera.

15. A method of obtaining a quantitative measure of quality of an image guided interventional procedure in which an interventional instrument is guided by an operator by reference to an image obtained by an imaging system and in which the position of the interventional instrument is tracked by a position tracking system, comprising:
- receiving position data representing the track of the interventional instrument during the image-guided interventional procedure from the position tracking system;
- recording the position data;
- processing the position data to derive one or more quantitative measures of the quality of the image-guided interventional procedure;
- displaying the one or more quantitative measures; and
- displaying a graphical plot of a position of a tip of the interventional instrument relative to an imaging plane of the imaging system against elapsed time in the procedure to show a trajectory of the tip, and color coding the trajectory according to a direction of movement of the interventional instrument, the color coding being such that a part of the trajectory when the tip is advancing towards the imaging plane is colored with a first color and a part of the trajectory when the tip is retreating from the imaging plane is colored with a second color, the first color being different from the second color, wherein:

the processing comprises deriving spatial or temporal measurements of a trajectory of the interventional instrument as said one or more quantitative measures, and wherein the quantitative measures are at least one of:

number of significant trajectory readjustments, number of excursions of the tip of the interventional instrument from the imaging plane of the imaging system, distance advanced by the tip of the interventional instrument during excursions from the imaging plane of the imaging system, number of incursions of the tip of the interventional instrument into the imaging plane of the imaging system, distance advanced through the imaging plane of the imaging system, number of times an imaging probe of the imaging system moved, puncture time, and number of punctures.

16. The method according to claim 15 further comprising:

receiving image data from the imaging system;

recording the image data; and processing the position data and image data to derive the one or more quantitative measures of the quality of the image-guided interventional procedure.

17. The method according to claim 16 comprising associating the position data and image data with time stamps to permit them to be mutually synchronized.

18. The method according to claim 15 comprising deriving spatial deviations from a predefined interventional instrument trajectory as said one or more quantitative measures or deriving temporal deviations from a predefined procedure timing as said one or more quantitative measures.

19. The method according to claim 15 comprising processing the position data to derive one or more information metrics relating to the image-guided procedure.

20. The method according to claim 19 wherein the information metrics comprise at least one of: procedure time, pre-puncture time, puncture time, insertion angle of the interventional instrument, direction of movement of the interventional instrument relative to the imaging probe of the imaging system.

21. The method according to claim 15 comprising display graphical plots of the one or more quantitative measures.

22. The method according to claim 15 wherein the imaging system is one of: an ultrasound imaging system, x-ray imaging system, magnetic resonance imaging system, a PET imaging system.

23. The method according to claim 15 wherein the position tracking system is one of: a magnetic position detection system, or an optical position detection system.

24. The method according to claim 15 wherein the position tracking system is a magnetic position detection system comprising magnetic field sensors mounted to the imaging probe of the imaging system and a magnetic field of the interventional instrument.

25. The method according to claim 15 comprising receiving image segmentation information relating to the structure of the subject of the image and deriving said one or more quantitative measures relative to the structure of the subject of the image.

26. The method according to claim 25 comprising processing the image obtained by the imaging system to automatically generate said image segmentation information.

27. The method according to claim 15 further receiving a video image of the operator conducting the image-guided interventional procedure and processing the video image to provide user eye motion tracking.

28. A computer program product embodied on a non-transitory computer readable medium for controlling a computer system to execute the method of claim 15.

* * * * *